United States Patent
Napoletano et al.

[11] Patent Number: 6,103,909
[45] Date of Patent: Aug. 15, 2000

[54] AZOLE COMPOUNDS ENDOWED WITH ANTIMYCOTIC ACTIVITY FOR HUMAN AND VETERINARY USE

[75] Inventors: Mauro Napoletano, Milan; Cristina Fraire, Legnano; Enrico Albini, Pavia; Giovanna Schioppacassi, Rho, all of Italy

[73] Assignee: Isagro S.p.A. and Zambon Group S.p.A., Milan, Italy

[21] Appl. No.: 09/138,904

[22] Filed: Aug. 24, 1998

Related U.S. Application Data

[62] Division of application No. 08/806,149, Feb. 25, 1997, Pat. No. 5,869,512.

[30] Foreign Application Priority Data

Feb. 28, 1996 [IT] Italy .................. MI96A0371

[51] Int. Cl.⁷ .................. C07D 233/60; C07D 249/08
[52] U.S. Cl. .................. 548/268.6; 548/342.1; 548/341.1
[58] Field of Search .................. 548/268.6, 342.1, 548/341.1

[56] References Cited

U.S. PATENT DOCUMENTS

| | | | |
|---|---|---|---|
| 4,929,631 | 5/1990 | Colle et al. .................. | 548/268.8 X |
| 5,021,442 | 6/1991 | Colle et al. .................. | 548/268.6 X |
| 5,081,138 | 1/1992 | Saji et al. .................. | 548/268.6 X |

OTHER PUBLICATIONS

Derwent Abstract, 96–476720, Week 9647, WO 9631490, Oct. 10, 1996.

*Primary Examiner*—Fiona T. Powers
*Attorney, Agent, or Firm*—Arent Fox Kintner Plotkin Kahn

[57] ABSTRACT

Compounds of formula

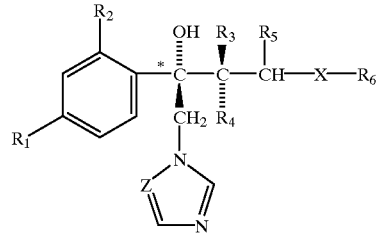

(II-A)

wherein $R_1$ is chloro, fluoro, bromo or trifluoromethyl;

$R_2$ is hydrogen, chloro, fluoro, bromo or trifluoromethyl;

Z is CH or N;

$R_3$, $R_4$ and $R_5$, which are the same or different, are hydrogen or $C_1$–$C_4$ alkyl, with the proviso that $R_4$ is different from $R_5$ when $R_3$ is hydrogen;

X is O, S, SO or $SO_2$;

$R_6$ is a $C_1$–$C_5$ polyfluoroalkyl group containing at least two fluorine atoms and optionally other halogen atoms selected from the group consisting of chloro and bromo; processes for their preparation and pharmaceutical compositions containing them are described.

The compounds of formula II-A are endowed with a marked wide range antimycotic acitivity.

4 Claims, No Drawings

AZOLE COMPOUNDS ENDOWED WITH ANTIMYCOTIC ACTIVITY FOR HUMAN AND VETERINARY USE

This application is a Divisional of application Ser. No. 08/806,149, filed Feb. 25, 1997. Now U.S. Pat. No. 5,869,512.

The present invention relates to antimycotic compounds for human and veterinary use, and particularly, relates to azole compounds endowed with antimycotic activity for the treatment and prophylaxis of infections in human and animals due to fungi and yeasts.

Among the antimycotic compounds known in literature an important class is composed by the so-called azole derivatives which embraces some compounds employed in therapy such as Fluconazole (The Merck Index, XI ed., No.4054, page 645), Itraconazole (The Merck Index, XI ed., No. 5131, page 825) and Ketoconazole (The Merck Index, XI ed., No. 5181, page 835).

However, as far as we know, no one of these compounds is endowed with a marked antimycotic activity against some opportunistic pathogenic fungal strains which cause infections even fatal for immuno-depressed patients.

Among the azole derivatives known as antimycotic for human or veterinary use a number of compounds characterised by the presence of a tertiary alcohol moiety in their formula

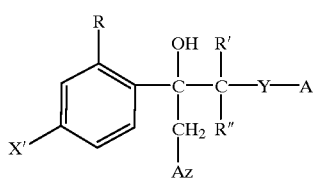

(I)

wherein Az represents a triazole or imidazole group, X' is preferably chloro, fluoro or trifluoromethyl, R is preferably hydrogen, chloro or fluoro, R' and R", which are the same or different, are hydrogen or alkyl groups, Y is S, SO, $SO_2$ or O, and A is alkyl; hereinafter named as tertiary alcohol azoles, are described.

Among these tertiary alcohol azoles we mention, for example, the compounds described in the European patent applications No. 54974 (Sumitomo Chemical Company Limited), No. 61835 (Imperial Chemical Industries PLC), No. 107392 (Pfizer Limited), No. 140154 (Sumitomo Chemical Company Limited), No. 178533 (Sumitomo Pharmaceutical Company Limited), No. 435081 (SS Pharmaceutical Co. Ltd.) and No. 473387 (Sankyo Company Limited).

For some of these compounds a marked antimycotic activity was disclosed, though generically sometimes, both topically and systemically. However, as far as we know, the only compound under development is the one known as Genaconazole, (2R,3R) α-(2,4-difluorophenyl)-α-[1-(methylsulfonyl)ethyl]-1H-1,2,4-triazol-1-ethanol, disclosed in the European patent application No. 178533.

Recently higher homologues of the tertiary alcohol azoles of formula I have been described in the European patent application No. 679647 (Nihon Nohyaku Co. Ltd.) as endowed with a good antimycotic activity against *Candida albicans*, and characterised in that A is an optionally substituted phenyl or heterocycle.

The International patent application No. WO 96/31490 in the name of the same applicants discloses the antimycotic activity of racemic mixtures of some azole compounds of formula II.

It has been now found that single enantiomers of the azole derivatives of formula

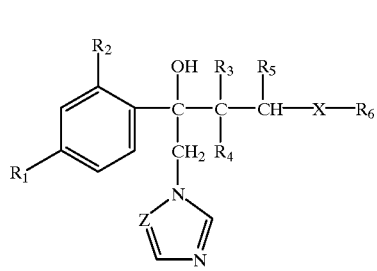

(II)

wherein
$R_1$ is chloro, fluoro, bromo or trifluoromethyl;
$R_2$ is hydrogen, chloro, fluoro, bromo or trifluoromethyl;
Z is CH or N;
$R_3$, $R_4$ and $R_5$, which are the same or different, are hydrogen or $C_1$–$C_4$ alkyl, with the proviso that $R_4$ is different from $R_5$ when $R_3$ is hydrogen;
X is O, S, SO or $SO_2$;
$R_6$ is a $C_1$–$C_5$ polyfluoroalkyl group containing at least two fluorine atoms and optionally other halogen atoms selected from the group consisting of chloro and bromo;

are endowed with a marked wide range antimycotic activity against fungi pathogenic for human and animals, particularly also against fungal strains resistant to antimycotics used in therapy, and against opportunistic pathogenic fungal strains causing infections in immuno-depressed subjects, and they are active both topically and systemically. Some of the compounds of formula II in racemic mixture, especially the ones wherein X is O or S, are comprised in the European patent application No. 315946 (Presidenza del Consiglio dei Ministri—Ufficio del Ministero per il Coordinamento delle Iniziative per la Ricerca Scientifica e Tecnologica) and said to be useful in agriculture as immunising agents against fungal pathologies and as phytogrowth regulators for useful growings.

Therefore object of the present invention are compounds of formula

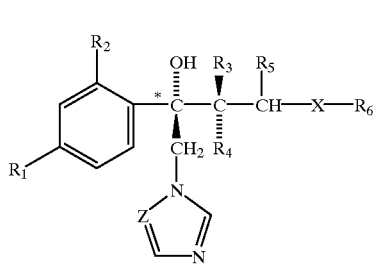

(II-A)

wherein
$R_1$ is chloro, fluoro, bromo or trifluoromethyl;
$R_2$ is hydrogen, chloro, fluoro, bromo or trifluoromethyl;
Z is CH o N;
$R_3$, $R_4$ and $R_5$, which are the same or different, are hydrogen or $C_1$–$C_4$ alkyl, with the proviso that $R_4$ is different from $R_5$ when $R_3$ is hydrogen;
X is O, S, SO or $SO_2$;
$R_6$ is a $C_1$–$C_5$ polyfluoroalkyl group containing at least two fluorine atoms and optionally other halogen atoms selected from the group consisting of chloro and bromo;

and the pharmaceutically acceptable acid salts thereof.

The proviso at formula II-A is made to exclude the compounds claimed in the European patent application No. 272679.

Another object of the present invention is constituted by compounds of formula II-A and the pharmaceutically acceptable salts thereof for use as a medicament.

The carbon atom marked with an asterisk has the absolute configuration defined in the formula. Thus according to the Cahn, Ingold and Prelog convention, the configuration of this carbon atom is R or S depending on the priority order of the substituents.

The compounds of formula II-A can also contain a second chiral centre when $R_3$ and $R_4$ are different one from the other, and thus be diastereoisomers. The diastereoisomers of formula II-A object of the invention are threo diastereoisomers.

The compounds of formula II-A are endowed with a powerful wide range antimycotic activity, particularly against Candida spp and *Cryptococcus neoformans* strains resistant to Fluconazole and Itraconazole, and against *Candida glabrata*, *Candida krusei*, Aspergillus spp and Fusarium spp resistant to Itraconazole and, like the previous ones, against pathogenic strains responsible of fungal infections in immuno-depressed patients, and are useful for the treatment and prophylaxis of fungal and yeast infections in human and animals.

The term $C_1$–$C_4$ alkyl for $R_3$, $R_4$ and $R_5$ means methyl, ethyl, n-propyl, isopropyl, n-butyl, isobutyl, sec-butyl and t.butyl groups, methyl and ethyl being preferred.

The term $C_1$–$C_5$ polyfluoroalkyl group containing at least two fluorine atoms preferably intends difluoromethyl, trifluoromethyl, 1,1,2-trifluoro-2-chloroethyl, 1,1-difluoroethyl, 2,2,2-trifluoroethyl, 1,1,2-trifluoroethyl, 1,1,2,2-tetrafluoroethyl, 1,1,2,3,3,3-hexafluoropropyl, 2,2,3,3-tetrafluoropropyl groups and the isomers thereof, the 1,1,2,2-tetrafluoroethyl group being the most preferred.

The salts of the compounds of formula II-A are salts with pharmaceutically acceptable organic and inorganic acids, such as hydrochloric, hydrobromic, hydroiodic, nitric, phosphoric, acetic, oxalic, malic, benzoic, benzenesulphonic, methansulphonic, 4-methyl-benzenesulphonic, fumaric, lactic, tartaric, citric and gluconic acid. Preferred compounds of formula II-A are the ones wherein $R_1$ is chloro or fluoro, $R_2$ is hydrogen, chloro or fluoro, $R_3$ is methyl or ethyl, $R_4$ and $R_5$, which are the same or different, are hydrogen, methyl or ethyl, Z is N and $R_6$ is a 1,1,2,2-tetrafluoroethyl group.

More preferred compounds of formula II-A are the ones wherein $R_1$ is chloro or fluoro, $R_2$ is hydrogen, chloro or fluoro, $R_3$ is methyl or ethyl, $R_4$ and $R_5$, which are the same or different are hydrogen, methyl or ethyl, Z is N, $R_6$ is a 1,1,2,2-tetrafluoroethyl group and X is O or $SO_2$.

Specific examples of the preferred compounds of formula II-A are the following:

(2R,3S) 1-(1H-1,2,4-triazolyl)-2-(2,4-difluorophenyl)-3-ethyl-4-(1,1,2,2,-tetrafluoro-ethoxy)-2-butanol (2R,3S) 1-(1H-1,2,4-triazolyl)-2-(2,4-dichlorophenyl)-3-methyl-4-(1,1,2,2-tetrafluoro-ethoxy)-2-butanol (2R,3R) 1-(1H-1,2,4-triazolyl)-2-(2,4-dichlorophenyl)-3-methyl-4-(1,1,2,2-tetrafluoro-ethylthio)-2-butanol (2R,3S) 1-(1H-1,2,4-triazolyl)-2-(2,4-difluorophenyl)-3-methyl-4-(1,1,2,2-tetrafluoro-ethoxy)-2-butanol (2R,3R) 1-(1H-1,2,4-triazolyl)-2-(2,4-difluorophenyl)-3-methyl-4-(1,1,2,2-tetrafluoro-ethylthio)-2-butanol (2R,3S) 1-(1H-1,2,4-triazolyl)-2-(4-chlorophenyl)-3-methyl-4-(1,1,2,2-tetrafluoro-ethoxy)-2-butanol (2R,3R) 1-(1H-1,2,4-triazolyl)-2-(4-chlorophenyl)-3-methyl-4-(1,1,2,2,-tetrafluoro-ethylthio)-2-butanol (2R) 1-(1H-1,2,4-triazolyl)-2-(2,4-difluorophenyl)-3,3-dimethyl-4(1,1,2,2,-tetrafluoro-ethoxy)-2-butanol (2R,3S) 1-(1H-1,2,4-triazolyl)-2-(4-fluorophenyl)-3-methyl-4-(1,1,2,2-tetrafluoro-ethoxy)-2-butanol (2R,3R) 1-(1H-1,2,4-triazolyl)-2-(4-fluorophenyl)-3-methyl-4-(1,1,2,2-tetrafluoro-ethylthio)2-butanol (2S) 1-(1H-1,2,4-triazolyl)-2-(4-chlorophenyl)-3,3-dimethyl-4-(1,1,2,2-tetrafluoro-ethoxy)-2-butanol (2S) 1-(1H-1,2,4-triazolyl)-2-(4-chlorophenyl)-3,3-dimethyl-4-(1,1,2,2-tetrafluoro-ethylthio)-2-butanol (2S) 1-(1H-1,2,4-triazolyl)-2-(4-fluorophenyl)-3,3-dimethyl-4-(1,1,2,2-tetrafluoro-ethoxy)-2-butanol (2S) 1-(1H-1,2,4-triazolyl)-2-(4-fluorophenyl)-3,3-dimethyl-4-(1,1,2,2-tetrafluoro-ethylthio)-2-butanol (2R,3R) 1-(1H-1,2,4-triazolyl)-2-(2,4-dichlorophenyl)-3-methyl-4-(1,1,2,2-tetrachloroethylsulfonyl)-2-butanol.

The preparation of the compounds of formula II-A wherein X is O or S may be carried out according to the synthetic scheme described in the already cited European patent application No. 315946 starting from the suitable intermediates in optically active form.

The compounds of formula II-A wherein X is SO or $SO_2$ may be obtained from the corresponding compounds of formula II-A wherein X is S following conventional oxidation techniques. Preferably hydrogen peroxide, hypohalides or peracids are employed as oxidising agents, optionally in the presence of catalysts. Preferably the preparation of the compounds of formula II-A wherein X is O or S is carried out by adding a polyfluoroolefin of formula

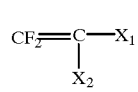
(III)

wherein $X_1$ and $X_2$, which are the same or different, are F, Cl or $CF_3$;

or by reacting a polyfluorinated alcohol of formula

(IV)

wherein $R_7$ is a $C_1$–$C_4$ polyfluoroalkyl group containing at least two fluorine atoms and optionally other halogen atoms selected from the group consisting of chloro and bromo;

with an optically active intermediate of formula

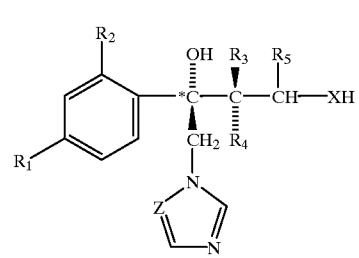
(V)

wherein $R_1$, $R_2$, $R_3$, $R_4$, $R_5$ and Z are as defined above, and X is O or S;

or with a reactive derivative thereof such as an ester, for example, a mesylate, tosylate or trifluoromethansulphonate.

The optically active intermediates of formula V may be prepared following known methods.

For example, the compounds of formula V may be prepared by the resolution of the corresponding racemic mixtures such as the ones described in the above cited European patent application No. 315946 or in the U.S. Pat. No. 5134152.

Alternatively, the compounds of formula V wherein X is S may be prepared from the corresponding compounds of formula V wherein X is O through known methods. Furthermore the enzymatic resolution by stereoselective acylation and subsequent hydrolysis was found particularly advantageous for preparing the compounds of formula V wherein X is O and $R_3$ and $R_4$ are both methyl.

Though the enzymatic resolution by stereoselective acylation is known for preparing the lower homologous tertiary alcohol of the compounds of formula V (see, for example, the International patent application WO 94/24305—Zeneca Limited), is surprising that it may also be applied for preparing the compounds of formula V wherein X is O and $R_3$ and $R_4$ are both methyl.

In fact, not only in these compounds there are two carbon atoms between the moiety to be acylated and the asymmetric carbon atom, but above all one of these carbon atoms is disubstituted thus bearing a conspicuous steric hindrance.

Therefore a further object of the present invention is a process for enzymatically resolving the compounds of formula V wherein X is O, and $R_3$ and $R_4$ are both methyl, process comprising their stereoselective acylation and subsequent hydrolysis.

Alternatively, the compounds of formula V wherein X is O and $R_5$ is a hydrogen atom may be prepared by reducing the corresponding acids of formula

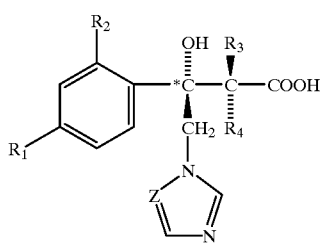

(VI)

wherein $R_1$, $R_2$, $R_3$, $R_4$ and Z are defined as above.

The compounds of formula VI are known or can be readily prepared according to known methods (Bartroli J. et al., J. Org. Chem. 1995, 60, 3000–3012).

The preparation of the salts of the compounds of formula II-A may be carried out according to conventional techniques, for example, by admixing in solution equimolar amounts of a compound of formula II-A and of the selected acid, and separating the salt by precipitation and filtration or evaporation of the solvent.

The compounds of formula II-A and their salts are antimycotic compounds useful in the treatment and prophylaxis of fungal and yeast infections in human and animals. Actually, the compounds of formula II-A object of the present invention are endowed with antimycotic activity against yeast, filamentosous fungi, dermatophytes and dimorphic fungi.

The antimycotic activity has been evaluated in vitro as $IC_{50}$ and as MIC (minimum inhibiting concentration) on a number of strains such as, for example, *Candida albicans, Cryptococcus neoformans, Trichophyton mentagrophytes, Aspergillus fumigatus, Candida parapsilosis, Candida lusitaniae, Candida kefyr, Candida tropicalis, Candida krusei, Candida glabrata, Aspergillus niger* and Fusarium spp.

It is important to underline that the compounds of formula II-A object of the present invention have shown to be effective against all the strains of Candida spp. and *Cryptococcus neoformans* taken into consideration, comprising the ones resistant to Fluconazole, Itraconazole and Genaconazole.

A particularly marked antimycotic activity was revealed also against strains of *Candida glabrata* and Fusarium spp., resistant to Itraconazole and Genaconazole, and against *Candida krusei* and *Aspergillus fumigatus*, resistant to Fluconazole and Genaconazole, all of them being pathogenic agents responsible for infections in immuno-depressed subjects.

The antimycotic activity of the compounds of formula II-A object of the present invention has been evaluated also in comparison with the one of the corresponding enantiomers.

In some cases the activity of these enantiomers was comparable with the one of the reference compounds, nevertheless it is overall markedly lower than the one of the compounds of formula II-A object of the present invention.

The in vivo antimycotic activity has been estimated, both intraperitoneally and orally, in a Candida model experimentally induced in mouse against *Candida albicans* strains sensible to Fluconazole and Itraconazole.

The 50% protective dose ($PD_{50}$) of the compounds of formula II-A has been determined in the in vivo tests and it showed to be at least comparable to the one of the reference compounds.

Therefore the compounds of formula II-A object of the present invention are active on wide range deep mycosis, but particularly against opportunistic pathogenic agents responsible of infections in immuno-depressed subjects, they are topically, orally and parenterally administrable and endowed with a good therapeutic index.

Then the compounds of formula II-A are useful in the human or veterinary treatment and prophylaxis of systemic and mucosal infections due to fungi and yeasts.

As just emphasised, the sound pharmacological activity of the compounds of formula II-A, shown also against strains resistant to antimycotics used in therapy and against recently isolated strains responsible of infections in immuno-depressed subjects, is particularly surprising considering that the compounds disclosed by the European patent application No. 315946 were said to be immunising agents for fungal pathologies and phytogrowth regulating agents on useful growings, both their activities being limited to the agricultural use.

The pharmacological activity of the compounds of formula II-A is still more surprising considering that such compounds, while showing some structural moieties in common with the azole tertiary alcohols described by the literature, are in the same time characterized by the presence of a two carbon atoms chain between the carbon atom bearing the hydroxy group and the oxygen or sulphur atom, and of a simple polyfluorinated alkyl in the ether or sulphur containing moiety.

As far as we know, the combination of these structural characteristics has never been described by the literature in the rank of the compounds of the azole tertiary alcohols class with antimycotic activity for human and animal use.

For the human and veterinary use the compounds of formula II-A may be administered in admixture with a suitable carrier selected in view of the administration route.

Therefore a further object of the present invention comprises pharmaceutical compositions containing a therapeutically effective amount of one of the compounds of formula II-A in admixture with a pharmaceutically acceptable carrier.

For example, the compounds of formula II-A or the salts thereof may be orally administered as tablets, capsules, solutions or suspensions.

As for the parenteral administration, for example via intravenous, intramuscular or subcutaneous route, the compounds of formula II-A or the salts thereof are in form of sterile aqueous solution.

Alternatively, the compounds of formula II-A or the salts thereof may be administered as suppositories or pessaries.

As for the topical administration, the compounds of formula II-A or the salts thereof are preferably formulated as creams or powders.

As for the oral or parenteral administration the daily dosage of the compound of formula II-A generally ranges between 0.1 and 50 mg/kg, preferably between 1 and 20 mg/kg, to be subdivided in one or more spaced out doses.

For better illustrating the present invention the following examples are provided.

EXAMPLE 1

Enzymatic Kynetic Resolution of (±) 3-(2,4-difluorophenyl)-2,2-dimethyl-4-(1H-1,2,4-triazol-1-yl)-1,3-butanediol a) Isomer (+)

The enzyme (3 g; lipase from *Candida cilindracea* type VII—Sigma) was added under vigorous stirring at 30° C. to a solution of (±) 3-(2,4-difluorophenyl)-2,2-dimethyl-4-(1H-1,2,4-triazol-1-yl)-1,3-butanediol (2,97 g; 10 mmoles) in chloroform (60 ml) and vinyl acetate (1.9 ml; 20 mmoles).

After 72 hours the suspension was filtered, and further enzyme was added (3 g) while maintaining under stirring at 30° C. for further 24 hours. The suspension was filtered, the solid washed with chloroform (20 ml) and the organic phase evaporated under reduced pressure.

The residue was chromatographed on silica gel (eluent ethyl acetate:hexane=60:40) to yield (−) 3-(2,4-difluorophenyl)-3-hydroxy-2,2-dimethyl-4-(1H-1,2,4-triazol-1-yl)butyl acetate (1.63 g; e.e. 88% chiral HPLC—column CHIRACEL-OD, eluent hexane:isopropanol=70:30) and (+) 3-(2,4-difluorophenyl)-2,2-dimethyl-4-(1H-1,2,4-triazol-1-yl)-1,3-butanediol (1.3 g; e.e. 79% chiral HPLC).

The isomer (+) thus obtained (1.3 g) was treated again under the same conditions with the lipase for 17 hours.

After the same treatment and isolation by flash chromatography (+) 3-(2,4-difluorophenyl)-2,2-dimethyl-4-(1H-1,2,4-triazol-1-yl)-1,3-butanediol (0.92 g; yield 62%) was obtained as a white solid.

$[\alpha]D^{20}$=+43.4° (c=1%, methanol); Chiral HPLC=e.e. 95%; m.p. 116.5–117.5° C.;

$^1$H-NMR identical to the one of the racemic mixture.

b) Isomer (−)

(−) 3-(2,4-difluorophenyl)-3-hydroxy-2,2-dimethyl-4-(1H-1,2,4-triazol-1-yl)butyl acetate obtained in the previous step (a) (1.63 g) was dissolved in a 0.05M pH 7 phosphate buffer (400 ml) and acetone (50 ml).

The solution under stirring at 30° C. was added with the enzyme (1.6 g; lipase from *Candida cilindracea* type VII) and the pH was maintained during the subsequent addition of 0.1 M sodium hydroxide.

After 5 hours pH was brought to 4 by concentrated hydrochloric acid and the extraction was effected with ethyl acetate (3×100 ml).

The organic phase was anhydrified over sodium sulphate and evaporated under reduced pressure to yield an oily residue.

After flash chromatography on silica gel (eluent ethyl acetate:hexane=60:40) (−) 3-(2,4-difluorophenyl)-2,2-dimethyl-4-(1H-1,2,4-triazol-1-yl)-1,3-butanediol (1.20 g; yield 80%) was isolated as a white solid.

$[\alpha]D^{20}$=−46.2° (c=1%, methanol); Chiral HPLC=e.e. 98.4%; m.p. 117–118° C.; $^1$H-NMR identical to the one of the racemic mixture.

EXAMPLE 2

Preparation of (−) (2S,3R)-3-(2,4-difluorophenyl)-2-methyl-4-(1H-1,2,4-triazol-1-yl)-1.3-butanediol A solution of (2R,3R)-3-(2,4-difluorophenyl)-3-hydroxy-2-methyl-4-(1H-1,2,4-triazol-1-yl)butanoic acid (0.88 g; 2.97 mmoles) in anhydrous tetrahydrofuran (6.5 ml) was dropwise added with boron trifluoroetherate (0.365 ml; 2.97 mmoles) and the mixture was refluxed for 30 minutes.

The resulting solution was dropwise added at 55° C. with a 10M solution of boranedimethylsulphide in tetrahydrofuran (0.356 ml; 3.56 mmoles) and the reflux was maintained for 6 hours.

After cooling to 4° C. a solution water:tetrahydrofuran=1:1 (3 ml) then 5M soda (8 ml) were added and the mixture was refluxed for 12 hours.

The tetrahydrofuran was evaporated under reduced pressure, the mixture was extracted with chloroform (5×10 ml), the organic phase was anhydrified and evaporated to yield a solid residue which was crystallised from benzene:hexane=1:1 (20 ml) to give (−) (2S,3R)-3-(2,4-difluorophenyl)-2-methyl-4-(1H-1,2,4-triazol-1-yl)-1,3-butanediol (0.76 g; yield 90%).

m.p. 93–95° C. $[\alpha]D^{20}$=−59.6° (c=1%, methanol); $^1$H-NMR (CDCl$_3$): 7.93 (s, 1H); 7.74 (s, 1H); 7.48–7.33 (m, 1H); 6.83–6.68 (m, 2H); 5.40 (s-broad, 1H); 4.97 (d, 1H); 4.78 (d, 1H); 4.00 (dd, 1H); 3.80 (dd, 1H); 3.10 (s-broad, 1H); 2.45–2.25 (m, 1H); 0.85 (d, 3H).

Similarly operating the following compounds were prepared.

(−) (2S,3R)-3-(2,4-dichlorophenyl)-2-methyl-4-(1H-1,2,4-triazol-1-yl)-1,3-butanediol yield 87%; m.p. 108–110° C.; $[\alpha]D^{20}$=−90.7° (c=1%, methanol).

(+) (2R,3 S)-3-(2,4-dichlorophenyl)-2-methyl-4-(1H-1,2,4-triazol-1-yl)-1,3-butanediol yield 91%; m.p. 110–111° C.; $[\alpha]D^{20}$=+87.0° (c=1%, methanol).

(−) (2S,3R)-2-ethyl-3-(2,4-difluorophenyl)-4-(1H-1,2,4-triazol-1-yl)-1,3-butanediol yield 90%; m.p. 75–77° C.; $[\alpha]D^{20}$=−41.1° (c=1%, methanol), Chiral HPLC (hexane:isopropanol=70:30)=e.e. 92%; $^1$H-NMR (CDCl$_3$): 7.89 and 7.71 (2s, 2H, 2CH-Triaz.); 7.40–6.62 (m, 3H, Ar); 5.30 (s-broad, 1H, OH); 4.98–4.70 (m, 2H, CH$_2$-Triaz.); 4.12–3.87 (m, 2H, CH$_2$—OH); 2.80 (s-broad, 1H, CH$_2$—OH); 2.05–1.93 (m, 2H, *CH—CH$_2$—CH$_3$); 1.60–0.98 (m, 2H, CH—*CH$_2$—CH$_3$); 0.81 (t, 3H, CH—CH$_2$—*CH$_3$).

EXAMPLE 3

Preparation of (−) 2-(2,4-difluorophenyl)-4-(1,1,2,2-tetrafluoroethoxy)-3,3-dimethyl-1-(1H-1,2,4-triazol-1-yl)-2-butanol (Compound 1A)

A solution of (−) 3-(2,4-difluorophenyl)-2,2-dimethyl-4-(1H-1,2,4-triazol-1-yl)-1,3-butanediol (5 g; 16.8 mmoles), prepared as described in Example 1, and dimethylsulphoxide (8 ml) in toluene (60 ml) under stirring at −5° C. was added with potassium hydroxide in dust (533 mg; 9.5 mmoles).

The reaction atmosphere was substituted with tetrafluoroethylene and the mixture was maintained under stirring at −5° C. for 90 minutes.

After an addition of water (120 ml), the organic phase was washed with 5% hydrochloric acid (80 ml) and treated with anhydrous sodium hydrocarbonate (6.5 g) under stirring for 30 minutes.

The liquid phase was filtered and the solvent evaporated under reduced pressure to yield an oily residue which was purified by flash chromatography (eluent hexane: ethyl acetate=6:4) to give the compound 1A (5.2 g; yield 79%) as a white solid.

$[\alpha]D^{20}$=−48.5° (c=1%, methanol); Chiral HPLC=e.e. ≧99.8%; m.p. 46–47° C.; $^1$H-NMR (CDCl$_3$): 8.01 (d, 1H, CH-Tetr.); 7.69 (s, 1H, CH-Cat); 7.63–6.56 (m, 3H, Ar); 5.70 (tt, 1H, JHF=53.4 Hz, CHF$_2$); 5.33 (s-broad, 1H, OH); 5.29–4.41 (m, 2H, CH$_2$-Triaz.); system AB: VA=4.19, VB=3.75, JAB=9.8 Hz, CH$_2$—O; 1.06 (d, 3H, JHF=2.4 Hz, CH$_3$); 0.98 (s, 3H, CH$_3$).

Similarly operating the following compounds were prepared.

(+) 2-(2,4-difluorophenyl)-4-(1,1,2,2-tetrafluoroethoxy)-3,3-dimethyl-1,2,4,-triazol-1-yl-)-2-butanol (Compound 1B)

yield 87%; $[\alpha]D^{20}$=−56.1° (c=1%, methanol); Chiral HPLC (hexane:isopropanol=90:10)=e.e. 99% nitrate (crystallized from isopropyl ether/acetonitrile); m.p. 89–91° C.; $^1$H-NMR (CDCl$_3$): 9.70 (s, 1H, CH-Triaz.); 8.05 (s, 1H, CH-Triaz.); 7.37–6.67 (m, 3H, Ar); 6.77 (s-broad, H$^+$); 5.80 (tt, 1H, JHF=52.6 Hz, CHF$_2$); system AB: Va=5.11, Vb=4.87, Jab=14.2 Hz, *CH$_2$-Triaz.; part AB of system ABX: Va=4.42, Vb=4.21, Jab=11.1 Hz, Jax=7.7 Hz, Jbx=2.6 Hz; CH$_2$—O; 2.41–2.30 (m, 1H, *CH—CH$_2$); 1.32–1.18 (m, 2H, CH—*CH$_2$); 0.83 (d, 3H, JHH=7.1 Hz, CH$_3$).

Example 4
In vitro Antimycotic Activity

The activity inhibiting the growth of mycetes has been evaluated by the macromethods of the scalar brothdilution in geometrical progression (M. R. McGinnis and M. G. Rinaldi, "Antimycotic drugs: mechanisms of action, drug resistance, susceptibility testing and assay of activity in biological fluids", in Antibiotic in Laboratory Medicine, Ed. V. Lorian, Baltimora 1991).

As coltural medium Yeast Nitrogen Base broth (YNB) and Sabouraud Dextrose broth (SDB) were employed for yeasts and moulds respectively.

The results obtained in SDB (after incubation at 28° C. for 7 days) are expressed as minimum inhibiting concentration (MIC) the growing of the mycetes, whereas the results obtained in YNB (after incubation at 35° C. for 48 hours) are expressed as concentration inhibiting at 50% (IC$_{50}$) the growing of the yeast. Fluconazole has been taken as reference compound.

In the following Tables the data of the in vitro antimycotic activity against *Candida albicans, Aspergillus fumigatus, Cryptococcus neoformans* and *Trichophyton mentagrophytes* of some representative compounds of formula II are set forth.

TABLE 1

In vitro antimycotic activity of the compounds 1A, 3A, their respective enantiomers 1B, 3B, the compound 2A and the reference compound Fluconazole against *C. albicans, C. neoformans, T. mentagrophytes* and *A. fumigatus*.

(+) (2S,3R)-2-(2,4-dichlorophenyl)-4-(1,1,2,2-tetrafluoroethoxy)-3-methyl-1-(1H-1,2,4-triazol-1-yl)-2-butanol (Compound 3B)

colourless oil—yield 63%; $[\alpha]D^{20}$=+76.5° (c=1%, methanol); Chiral HPLC (hexane:isopropanol=90:10)=e.e. 99.8% nitrate (crystallised from isopropyl ether); m.p. 120.9–121.9° C.; $^1$H-NMR (CDCl$_3$): 9.67 and 8.05 (2s, 2H, Triaz.); 8.21 (s-broad, 2H, OH e HNO$_3$); 7.44 (d, 1H, JHH=8.6 Hz, C—*CH—CH—C—Cl); 7.35 (d, 1H, JHH=2.2 Hz, C—Cl—CH—C—Cl); 7.09 (dd, 1H, C—CH—*CH—C—Cl); 5.82 (tt, 1H, JHF=52.8 Hz, CHF$_2$); system AB: Va=5.67, Vb=4.89, Jab=14.3 Hz, *CH$_2$-Triaz.; part AB of system ABX: Va=4.44, Vb=4.09, Jab=10.8 Hz, Jax=8.4 Hz, Jbx=4.0 Hz; CH$_2$—O; 3.32–3.16 (m, 1H, *CH—CH$_3$); 0.71 (d, 3H, JHH=7.0 Hz, *CH$_3$—CH).

(−) (2R,3S)-3-etil-2-(2,4-difluorophenyl)-4-(1,1,2,2-tetrafluoroethoxy)-1-(1H-1,2,4-triazol-1-yl)-2-butanol (Compound 4A)

yield 87%; $[\alpha]D^{20}$=−56.1° (c=1%, methanol); Chiral HPLC (hexane:isopropanol=90:10)=e.e. 99% nitrate (crystallised from isopropyl ether/acetonitrile); m.p. 89–91° C.; $^1$H-NMR (CDCl$_3$): 9.70 (s, 1H, CH-Triaz.); 8.05 (s, 1H, CH-Triaz.); 7.37–6.67 (m, 3H, Ar); 6.77 (s-broad, H$^+$); 5.80 (tt, 1H, JHF=52.6 Hz, CHF$_2$); system AB: Va=5.11, Vb=4.87, Jab=14.2 Hz, *CH$_2$-Triaz.; part AB of system ABX: Va=4.42, Vb=4.21, Jab=11.1 Hz, Jax=7.7 Hz, Jbx=2.6 Hz; CH$_2$—O; 2.41–2.30 (m, 1H, *CH—CH$_2$); 1.32–1.18 (m 2H, CH—*CH$_2$); 0.83 (d, 3H, JHH=7.1 Hz, CH$_3$).

EXAMPLE 4

Preparation of (−) (2R,3S)-2-(2,4-dichlorophenyl)-4-(1,1,2,2-tetrafluoroethoxy)-3-methyl-1-(1H-1,2,4-triazol-1-yl)-2-butanol (Compound 3A)

Alternatively to the purification procedure of Example 3, the title compound as a crude (86.2 g) was dissolved in 173 ml of ethanol at a temperature comprised between 30 and 35° C., then filtered to obtain a perfectly clear solution which was dropped, at 20° C. in 90 minutes, into a mixture of water (260 ml) and ethanol (87 ml).

The mixture was heated to 35° C. kept under stirring for 90 minutes, cooled to 2° C. and again stirred for 60 minutes.

The insoluble solid was filtered, washed with a mixture ethanol/water 1:1 and dried in a oven under vacuum at 50° C. till a constant weight, thus yielding 74 g of (−) (2R,3S)-2-(2,4-dichlorophenyl)-4-(1,1,2,2-tetrafluoroethoxy)-3-methyl-1-(1H-1,2,4-triazol-1-yl)-2-butanol (Compound 3A) with a purity >99%;

$[\alpha]D^{22}$=−83.6 (c=1%, methanol); Chiral HPLC (hexane:isopropanol=90:10)=e.e. 99,5%; m.p. 79–80° C.; $^1$H-NMR (CDCl$_3$): 7.80 and 8.05 (2s, 2H, Triaz.); 7.42 (d, 1H, JHH=8.6 Hz, C—*CH—CH—C—Cl); 7.27 (d, 1H, JHH=2.1 Hz, C—Cl—CH—C—Cl); 7.05 (dd, 1H, C—CH—*CH—C—Cl); 5.75 (tt, 1H, JHF=53.4 Hz, CHF$_2$); system AB=VA=5.48, VB=4.54, JAB=14.4 Hz, *CH$_2$-Triaz.); 5.09 (broad signal, 1H, OH); 4.54–3.98 (m, 2H, CH$_2$—O); 3.14–2.97 (m, 1H, *CH—CH$_3$); 0.67 (d, 3H, JHH=7.1 Hz, *CH$_3$—CH).

EXAMPLE 5

Preparation of 3-(2,4-dichlorophenyl)-3-hydroxy-2-methyl-4-(1H, 1,2,4-triazol-1-yl)methansulphonic acid butyl ester A solution of (+) (2R,3S)-3-(2,4-dichlorophenyl)-2-methyl-4-(1H-1,2,4-triazol-1-yl)-1,3-butandiol (2.95 g; 9.31 mmoles), prepared as described in Example 2, in methylene chloride (90 ml) was added, under nitrogen atmosphere, firstly with triethylamine (1.94 ml; 13.9 mmoles), then with mesyl chloride (0.735 ml; 9.46 mmoles) at 0° C.

The reaction was carried out for 20 minutes while maintaining the temperature at 0° C., then the reaction mixture was poured into water (60 ml).

The phases were separated and the aqueous one was further extracted twice with methylene chloride.

The collected organic phases were washed with a 5% aqueous solution of sodium hydrocarbonate, then a saturated aqueous solution of sodium chloride, and anhydrified over sodium sulphate.

The solvent evaporation yielded 3.64 g (100%) of 3-(2,4-dichlorophenyl)-3-hydroxy-2-methyl-4-(1H-1,2,4-triazol-1-yl)methansulphonic acid butyl ester as a white solid which was used as such in the next step.

$^{1}$H-NMR (CDCl$_3$): 7.84 and 7.79 (2s, 2H, H-Triaz.); 7.50–7.00 (m, 3H, H-phenyl); 5.56 and 4.56 (2d, 2H, CH$_2$-Triaz.); 4.77 and 4.28 (2dd, 2H, CH$_2$-OMs); 3.20–3.10 (m, 1H, CH); 3.10 (s, 3H, CH$_3$ mesylate); 0.70 (d, 3H, CH$_3$).

EXAMPLE 6

Preparation of thioacetic acid S-[3-(2,4-dichlorophenyl)-3-hydroxy-2-methyl-4-(1H-1,2,4-triazol-1-yl)butyl] ester 3-(2,4-dichlorophenyl)-3-hydroxy-2-methyl-4-(1H-1,2,4-triazol-1-yl)methansulphonic acid butyl ester (9.3 mmoles), prepared as described in Example 5, was dissolved in ethanol (95 ml) and added with potassium thioacetate (2.12 g). The mixture was refluxed for 2 hours, then cooled in ice and the resulting precipitate was filtered and washed with iced methylene chloride. The filtrate was concentrated under reduced pressure, taken up with water (60 ml) and extracted more times with methylene chloride. The organic phases were collected and anhydrified over sodium sulphate, thus yielding 3.5 g of a reddish crude which was purified by flash chromatography on silica gel (eluent ethyl acetate:hexane= 1:1) thus yielding 1.72 (49%) of thioacetic acid S-[3-(2,4-dichlorophenyl)-3-hydroxy-2-methyl-4-(1H-1,2,4-triazol-1-yl)butyl] ester.

$^{1}$H-NMR (CDCl$_3$): 7.85 and 7.76 (2s, 2H, H-Triaz.); 7.50–7.00 (m, 3H, H-phenyl); 5.62 and 4.75 (2d, 2H, CH$_2$-Triaz.); 3.60–3.45 and 2.80–2.65 (2m, 2H, CH$_2$—SCOCH$_3$); 2.75 (m, 1H, CH); 2.39 (s, 3H, CH$_3$ thioacetate); 0.70 (d, 3H, CH$_3$).

EXAMPLE 7

Preparation of (2R,3R)-3-(2,4-dichlorophenyl)-3-hydroxy-2-methyl-4-(1H-1,2,4-triazol-1-yl)-1-butanthiol Under nitrogen atmosphere at room temperature a solution of potassium hydroxide (0.266 g; 4,74 mmoles) in methanol (40 ml) was dropped into a solution of thioacetic acid S-[3-(2,4-dichlorophenyl)-3-hydroxy-2-methyl-4-(1H-1,2,4-triazol-1-yl)butyl] ester, prepared as described in Example 6 (1.72 g; 4.6 mmoles) in methanol (40 ml).

After reacting for 10 minutes the reaction was quenched with 5% HCl (4 ml) diluted with water (20 ml), and the reaction mixture was concentrated under reduced pressure, then further diluted with water and extracted more times with methylene chloride. The anhydrification and evaporation of the collected organic phases yielded 1.6 g of a crude which was purified by flash chromatography of silica gel (eluent ethyl acetate:hexane=1:1). There was thus obtained 1.2 g (80%) of (2R,3R)-3-(2,4-dichlorophenyl)-3-hydroxy-2-methyl-4-(1H-1,2,4-triazol-1-yl)-1-butanthiol as a light oil.

$^{1}$H-NMR (CDCl$_3$): 7.85 and 7.79 (2s, 2H, H-Triaz.); 7.50–7.00 (m, 3H, H-phenyl); 5.55 and 4.60 (2d, 2H, CH$_2$-Triaz.); 3.10–2.90 and 2.80–2.60 (2m, 2H, CH$_2$—SH); 2.75 (m, 1H, CH); 1.58 (t, 1H, SH); 0.78 (d, 3H, CH$_3$).

EXAMPLE 8

Preparation of (−) (2R,3R)-2-(2,4-dichlorophenyl)-3-methyl-4-(1,1,2,2-tetrafluoroethylthio)-1-(1H-1,2,4-triazol-1-yl)-2-butanol (Compound 5)

Starting from (2R,3R)-3-(2,4-dichlorophenyl)-3-hydroxy-2-methyl-4-(1H-1,2,4-triazol-1-yl)-1-butanthiol (1.85 g; 5.57 mmoles), prepared as described in Example 7, and following the procedure of Example 3, there was obtained a crude which was purified by flash chromatography (eluent petroleum ether: ethyl acetate 6:4) to give 2, 15 g of (−) (2R,3R)-2-(2,4-dichlorophenyl)-3-methyl-4-(1,1,2,2-tetrafluoroethylthio)-1-(1H-1,2,4-triazol-1-yl)-2-butanol (Compound 5) as a white solid.

[α]D$^{22}$=−105.7° (c=1%, methanol); Chiral HPLC (hexane:isopropanol=90:10)=e.e. 99.78%; m.p. 61–63° C. $^{1}$H-NMR (CDCl$_3$): 7.84 (s, 1H, CH-Triaz.); 7.75 (s, 1H, CH-Triaz.); 7.43 (d, 1H, JHH=8.6 Hz, *CH—CH—CCl); 7.265 (d, 1H, JHH=2 Hz, Cl—C—CH—C—Cl); 7.08 (dd, 1H, CH—*CH—CCl); 5.83 (tt, 1H, JHF=53.8 Hz, CHF$_2$); system AB=Va=5.50, Vb=4.57, JAB=14.0 Hz, CH$_2$-Triaz.); 5.06 (broad signal, 1H, OH); 3.47–3.35 (m, 1H, *CH—CH$_3$); 3.07–2.90 (m, 2H, CH$_2$—S); 0.77 (d, 3H, JHH=6.3 Hz,*CH$_3$—CH).

EXAMPLE 9

Preparation of (−) (2R,3R)-2-(2,4-dichlorophenyl)-3-methyl-4-(1,1,2,2-tetrafluoroethyisulphinyl)-1-(1H-1,2,4-triazol-1-yl)-2-butanol (Compound 6)

A solution of (−) (2R,3R)-2-(2,4-dichlorophenyl)-3-methyl-4-(1,1,2,2-tetrafluoroethylthio)-1-(1H-1,2,4-triazol-1-yl)-2-butanol (0.48 g; 1.11 mmole), prepared as described in Example 8, in methanol (2.5 ml) was added with 40% hydrogen peroxide (0.073 ml; 0.89 mmole) in the presence of a catalytic amount of Na$_2$WO$_4$.2H$_2$O and left under stirring at room temperature for 3 days, then the reaction mixture was treated with sodium pyrosulphate (Na$_2$S$_2$O$_5$) in water, and basified with 10% sodium hydroxide.

The mixture was extracted with ether, dried and concentrated under vacuum to yield 0.41 g of an oil which was purified by flash chromatography (eluent ethyl acetate: petroleum ether 4:6).

The resulting oil (0.35 g) was dissolved in ethanol and treated with 70% nitric acid.

The mixture was concentrated under vacuum and gave a solid which was crumbled with warm isopropyl ether to yield 0.32 g of (−) (2R,3R)-2-(2,4-dichlorophenyl)-3-methyl-4-(1,1,2,2-tetrafluoroethylsulphinyl)-1-(1H-1,2,4-triazol-1-yl)-2-butanol (Compound 6) as a white solid.

m.p. 153–155° C.; $^{1}$H-NMR (CDCl$_3$): 9.56 and 9.51 (2s, 1H, CH-Triaz.); 8.13 and 8.10 (2s, 1H, CH-Triaz.); 7.58 (s-broad, H+); 7.50–7.08 (m, 3H, Ar); 6.57–5.98 (m, 1H, CHF$_2$); 5.66–4.87 (m, 2H, CH$_2$-Triaz; 3.57–2.79 (m, 3H, *CH—CH$_3$); 3.07–2.90 (m, 2H, CH$_2$—S); 0.77 (d, 3H, JHH=6.3 Hz,*CH$_3$—CH).

EXAMPLE 10

Preparation of (−) (2R,3R)-2-(2,4-dichlorophenyl)-3-methyl-4-(1,1,2,2-tetrachloroethylsulfonyl)-1-(1H-1,2,4-triazol-1-yl)-2-butanol (Compound 7)

A solution of (−) (2R,3R)-2-(2,4-dichlorophenyl)-3-methyl-4-(1,1,2,2-tetrafluoroethylthio)-1-(1H-1,2,4-triazol-1-yl)-2-butanol (0.5 g; 1.15 mmole), prepared as described in Example 8, in methanol (2.5 ml), in the presence of a catalytic amount of Na$_2$WO$_4$. 2H$_2$O and concentrated HCl (0.19 ml; 2.3 mmoles) was added with 40% hydrogen peroxide (0.9 ml; 10.35 mmoles) and heated to 60° C. for 14 hours, then left at room temperature overnight.

The reaction mixture was treated with a solution of sodium pyrosulphate (Na$_2$S$_2$O$_5$), basified with 10% sodium hydroxide, and extracted with ether, dried and concentrated under vacuum to yield 0.49 g of an oil which was purified by flash chromatography (eluent ethyl acetate: petroleum ether 1:1).

The resulting oil (0.45 g) was dissolved in ethanol and treated with 70% nitric acid.

The mixture was concentrated under vacuum and gave 0.42 g of (−) (2R,3R)-2-(2,4-dichloro-phenyl)-3-methyl-4-(1,1,2,2-tetrachloroethylsulfonyl)-1-(1H-1,2,4-triazol-1-yl)-2-butanol (Compound 7) as a white solid.

$[\alpha]D^{22}$=−63.4° (c=1%, methanol); Chiral HPLC (hexane:isopropanol=90:10)=e.e. 99.7%; m.p. 192–194° C.

$^1$H-NMR (CDCl$_3$): 8.52 (s, 1H, CH-Triaz.); 7.84 (s, 1H, CH-Triaz.); 7.58–7.25 (m, 3H, Ar); 7.19 (dt, 1H, JHF=51 Hz, CHF$_2$); 6.51–6.30 (broad signal H+); 5.10–4.74 (m, 2H, *CH$_2$-Triaz. -AB system); 4.10–3.39 (m, 1H, *CH$_2$—*CH$_3$); 0.84 (2d, 3H, JHH=6.1 Hz, CH$_3$).

EXAMPLE 11

In vitro Antimycotic Activity

A) The activity inhibiting the growth of mycetes has been evaluated by the macromethods of the scalar broth dilution in geometrical progression (M. R. McGinnis and M. G. Rinaldi, "Antimycotic drugs: mechanisms of action, drug resistance, susceptibility testing and assay of activity in biological fluids", in Antibiotic in Laboratory Medicine, Ed. V. Lorian, Baltimore 1991).

As growing medium Yeast Nitrogen Base broth (YNB) and Sabouraud Dextrose broth (SDB) were employed for yeasts and moulds respectively.

The results obtained in SDB (after incubation at 28° C. for 7 days) are expressed as minimum inhibiting concentration (MIC) the growing of the mycetes, whereas the results obtained in YNB (after incubation at 35° C. for 48 hours) are expressed as concentration inhibiting at 50% (IC$_{50}$) the growing of the yeast.

Fluconazole has been taken as reference compound.

In the following Table the data of the in vitro antimycotic activity against *Candida albicans, Aspergillus fumigatus, Cryptococcus neoformans* and *Trichophyton mentagrophytes* of some representative compounds of formula II are set forth.

TABLE 1a

In vitro antimycotic activity of the compounds 1A, 3A, their respective enantiomers 1B, 3B, the compound 2A and the reference compound Fluconazole against *C. albicans, C. neoformans, T. mentagrophytes* and *A. fumigatus.*

| | IC$_{50}$ (μg/ml) | | MIC (μg/ml) | |
|---|---|---|---|---|
| Compound | C. albicans 1040 | C. neoformans | T. mentagrophytes | A fumigatus |
| 1A | 0.0078 | 0.0078 | 0.125 | 4 |
| 1B | 1 | 1 | 32 | >128 |
| 2A(*) | 0.0312 | 0.0312 | 0.25 | 8 |
| 3A(*) | 0.0078 | 0.0078 | 0.0625 | 2 |
| 3B(*) | 0.25 | 1 | 16 | >128 |
| Fluconazole | 0.5 | 2 | 16 | >128 |

(*)the compounds were tested as nitrates.

The data set forth in the table show that the compounds object of the present invention have an antimycotic activity markedly higher than the one of the reference compound.

B) The activity inhibiting the growth of yeasts and filamentosous fungi has been evaluated by the method of the dilution in agar. The minimum inhibiting concentration at 50% (MIC$_{50}$) was measured by incorporating into the growing medium decreasing concentrations of the tested compounds thus yielding scalar concentration on basis 2, from 64 to 0.00085 μg/ml.

As growing medium casitone agar buffered at pH=7 (casitone 9 g, glucose 20 g, sodium citrate 10 g, leaven extract 5 g, agar 18 g, potassium biphosphate 0.54 g, sodium biphosphate 3.34 g, distilled water 1,000 ml) was employed.

For evaluating the activity against the yeasts the growing mediums containing the scalar concentrations of the compounds to be tested were inoculated with 1 μl of a suspension of 5×10$^5$ of blastospores/ml obtained from 24–48 hours cultures on Sabourad glucosate agar. The inoculated growing mediums were incubated at 32° C. and the measurements were effected after 24, 48 hours, after 72 hours for the slow growing yeasts such as the *Cryptococcus neoformans*

Fluconazole and Itraconazole have been taken as reference compounds.

In the following Table the data of the in vitro antimycotic activity against *Candida albicans, Candida tropicalis, Candida krusei, Candida glabrata, Candida parapsilosis, Candida lutitanice, Candida kefyr, Cryptococcus neoformans,* Trichosporon spp, *Blastoschizomyces capitatus,* Geotrichum spp, *Prototecha wicherhamii.*

TABLE 1b

In vitro antimycotic activity expressed as MIC$_{50}$ of the compounds 3A and 2A, and of the reference compounds Fluconazole and Itraconazole against the listed yeasts.

| | MIC$_{50}$ (μg/ml) | | | |
|---|---|---|---|---|
| Strains | Compound 2A | Compound 3A | Fluconazole | Itraconazole |
| C. albicans | 0.015 | 0.015 | 2 | 0.015 |
| C. tropicalis | 0.06 | 0.03 | 4 | 0.03 |
| C. krusei | 0.12 | 0.007 | 16 | 0.03 |
| C. glabrata | 0.12 | 0.12 | 16 | 4 |
| C. parapsilosis | 0.007 | 0.007 | 2 | <0.03 |
| C. lusitanie | 0.015 | 0.035 | 1 | 0.03 |
| C. kefyr | 0.017 | 0.017 | 1 | <0.03 |
| C. neoformans | 0.06 | 0.06 | 16 | 0.12 |
| Trichosporum spp | 0.06 | 0.12 | 16 | 0.12 |
| B. capitatus | 0.25 | 0.06 | 8 | 0.25 |
| Geotrichum spp | 0.5 | 0.12 | 16 | 0.1 |
| P. wicherhamii | 2 | 0.5 | >64 | — |

For evaluating the activity against the mycetes the growing mediums containing the scalar concentrations of the compounds to be tested were inoculated with 1 μl of a suspension of 5×10$^5$ of spores/ml (conides or endospores) obtained from duly sporulated coltures. The inoculated growing mediums were incubated at 32° C. and the measurements were effected after 1, 2, 3, 5, 7 and 10 days.

Fluconazole, Itraconazole and Amphotericin B have been taken as reference compounds.

In the following Table the data of the in vitro antimycotic activity against *Aspergillus fumigatus, Aspergillus flavus, Aspergillus niger, Aspergillus terreus, Aspergillus alliaceus, Fusariuim verticilloides, Fusarium proliferatum,* Pseudoallescheria, *Absidia corymbifera,* Mucor, *Rhyzomucor pusillus,* Acremonium, Trichoderma.

TABLE 1c

In vitro antimycotic activity expressed as MIC$_{50}$ of the compounds 3A and 2A, and of the reference compounds Fluconazole, Itraconazole and Amphotericin B against the listed fungi.

| Strains | Compound 2A | Compound 3A | Fluconazole | Itraconazole | Amphotericin B |
|---|---|---|---|---|---|
| A. fumigatus | 0.5 | 0.5 | >64 | 0.03 | 0.25 |
| A. flavusalis | 2 | 0.5 | >6 | 0.016 | 0.25 |
| A. niger | 0.06 | 0.03 | >64 | 0.016 | 0.12 |
| A. terreus | 0.25 | 0.12 | >64 | 0.016 | 0.25 |
| A. alliaceus | 0.5 | 0.12 | >64 | 0.016 | 16 |
| F. verticilloides | 0.12 | 0.12 | >64 | >8 | 2 |
| F. proliferatum | 0.25 | 0.25 | >64 | >8 | 1 |
| Pseudoallescheria | 0.06 | 0.06 | >64 | >16 | 3 |
| A. corymbifera | 0.25 | 0.06 | — | 0.03 | 0.06 |
| Mucor | 2 | 0.5 | >64 | >16 | 0.03 |
| R. pusillus | 0.25 | 0.016 | >64 | 0.16 | 0.06 |
| Acremonium | 4 | 4 | — | >16 | 16 |
| Trichoderma | 0.25 | 0.12 | — | 16 | 1 |

The data set forth in the tables show that the compounds object of the present invention have an overall antimycotic activity markedly higher than the one of the reference compounds.

TABLE 2

Oral antimycotic effectiveness of the compounds 1A, 3A, their respective enantiomers 1B, 3B, the compound 2A and the reference compounds Fluconazole and Itraconazole, expressed as medium protective dose (PD$_{50}$) after 14 days from the infection.

| | | PD$_{50}$ (mg/kg/os) at the 14$^{th}$ day | | | | | | |
|---|---|---|---|---|---|---|---|---|
| Experimental disease | Organism | Compound 1A | Compound 1B | Compound 2A$^{(a)}$ | Compound 3A$^{(a)}$ | Compound 3B$^{(a)}$ | Fluconazole | Itraconazole |
| Systemic candidiasis | Candida albicans 1040 | 0.64 | >2 | 0.32 | 0.38 | 4.57 | 0.61 | 1.74 |
| Systemic cryptococcosis | Cryptococcus neoformans 3443 | — | — | 8.84 | 5.48 | — | 63.16 | >50 |
| Intracranial cryptococcosis | Cryptococcus neoformans ISM | — | — | 14.59 | 12.5 | — | 22.28 | >25 |
| Pulmonary aspergillosis | Aspergillus fumigatus MOL-4 | — | — | 9.3 | 6.9 | — | >100 | >20 |
| Systemic aspergillosis | Aspergillus fumigatus MOL-4 | — | — | 3.5 | 4.5 | — | — | 10.2 |

EXAMPLE 12

In vivo Antimycotic Activity

Albino Charles River mice (CD1 strain) weighing from 23 to 25 g, normally feed with a standard diet and water ad libitum were employed.

Each animal has been intravenously (for systemic candidiasis, crytpococcosis, aspergillosis), intracranially (for intracranial cryptococcosis) or nasally (for pulmonary aspergillosis) treated with a suspension (0.2 ml containing 2.5×10$^7$ cells/ml) of the due microorganism in physiological. Right after the injection and after 4, 24 and 48 hours the animals has been orally administered (in 2% Arabic gum) geometrically progressive increasing doses of the compound under test. An infected group has been used as control.

The mortality monitoring of the mice has been prolonged up to 14 days. The medium protective dose (PD$_{50}$) has been calculated by the probits analysis (L. Lison—"Statistica applicata alla biologia sperimentale. La programmazione dell'esperimento e l'analisi dei risultati"—Casa Editrice Ambrosiana, 1961) on the basis of the number of animals survived at each concentration.

Fluconazole and Itraconazole were taken as reference compounds.

The following Table set forth the data of in vivo antimycotic activity of some compounds representative of the invention after in vivo administration.

The set forth data demonstrate that the compounds of formula II object of the present invention are active after oral administration at a medium protective dose lower then the one of Itraconazole and at least equivalent to the one of Fluconazole.

What we claim is:

1. A compound of formula

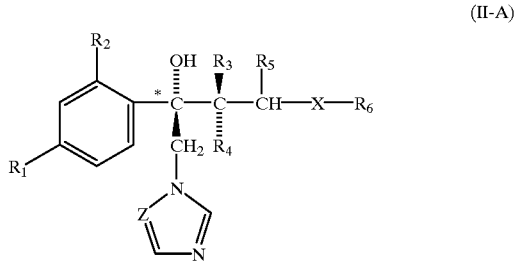

(II-A)

wherein
  $R_1$ is chloro, fluoro, bromo or trifluoromethyl;
  $R_2$ is hydrogen, chloro, fluoro, bromo or trifluoromethyl;
  Z is CH or N;

$R_3$, $R_4$ and $R_5$, which are the same or different, are hydrogen or $C_1$–$C_4$ alkyl, with the proviso that $R_4$ is different from $R_5$ when $R_3$ is hydrogen;

X is O, S, SO or $SO_2$;

$R_6$ is a $C_1$–$C_5$ polyfluoroalkyl group containing at least two fluorine atoms and optionally other halogen atoms selected from the group consisting of chloro and bromo;

and the pharmaceutically acceptable acid salts thereof.

2. A compound according to claim 1 wherein $R_1$ is chloro or fluoro, $R_2$ is hydrogen, chloro or fluoro, $R_3$ is methyl or ethyl, $R_4$ and $R_5$, which are the same or different, are hydrogen, methyl or ethyl, Z is N and $R_6$ is a 1,1,2,2-tetrafluoroethyl group.

3. A compound according to claim 2 wherein $R_1$ is chloro or fluoro, $R_2$ is hydrogen, chloro or fluoro, $R_3$ is methyl or ethyl, $R_4$ and $R_5$, which are the same or different, are hydrogen, methyl or ethyl, Z is N, $R_6$ is a 1,1,2,2-tetrafluoroethyl group and X is O or $SO_2$.

4. A process for the preparation of a compound according to claim 1 by reacting a polyfluoroolefin of formula

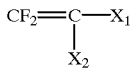

wherein $X_1$ and $X_2$, which are the same or different, are F, Cl or $CF_3$;

or by reacting a polyfluorinated alcohol of formula

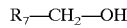  (IV)

wherein $R_7$ is a $C_1$–$C_4$ polyfluoroalkyl group containing at least two fluorine atoms and optionally other halogen atoms selected from the group consisting of chloro and bromo;

with an optically active intermediate of formula

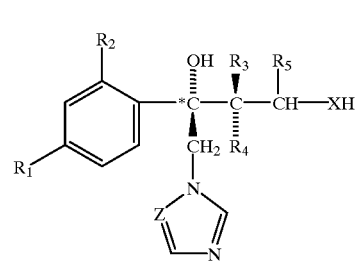  (V)

wherein $R_1$, $R_2$, $R_3$, $R_4$, $R_5$ and Z have the same meanings of claim 1, and X is O or S;

or a reactive derivative thereof, optionally followed by an oxidation.

* * * * *